United States Patent
Ding

(10) Patent No.: US 8,603,183 B2
(45) Date of Patent: Dec. 10, 2013

(54) BILAYERED BONE GRAFT DEVICE

(76) Inventor: Shinn Jyh Ding, Taichung (TW)

(*) Notice: Subject to any disclaimer, the term of this patent is extended or adjusted under 35 U.S.C. 154(b) by 34 days.

(21) Appl. No.: 13/166,090

(22) Filed: Jun. 22, 2011

(65) Prior Publication Data

US 2012/0330434 A1   Dec. 27, 2012

(51) Int. Cl.
*A61F 2/28* (2006.01)

(52) U.S. Cl.
USPC ............... 623/23.51; 623/23.56; 623/23.61

(58) Field of Classification Search
USPC .............. 623/23.51, 23.56, 23.58, 23.61
See application file for complete search history.

(56) References Cited

U.S. PATENT DOCUMENTS

| | | | |
|---|---|---|---|
| 2003/0120348 A1* | 6/2003 | Brosnahan et al. | 623/23.5 |
| 2004/0078085 A1* | 4/2004 | Pointillart et al. | 623/23.51 |
| 2007/0073401 A1* | 3/2007 | Pointillart et al. | 623/17.11 |
| 2008/0033572 A1* | 2/2008 | D'Antonio et al. | 623/23.51 |
| 2009/0198345 A1* | 8/2009 | Ding | 623/23.62 |
| 2010/0145469 A1* | 6/2010 | Barralet et al. | 623/23.56 |

OTHER PUBLICATIONS

Funishiro et al., "Preparation and compressive strength of alpha-tricalcium phosphate/gelatin gel composite cement", Mar. 2001, J. Biomed. Mater. Res., 54 (4): pp. 525-530.*

Bigi et al., "A biomimetic gelatin-calcium phosphate bone cement", Sep. 2004, The International journal of artifial organs, 27(8): pp. 664-673 (Abstract only provided).*
Ding, Shinn-Jyh et al., Bio-Inspired Calcium Silicate-gelatin Bone Grafts for Loan-Bearing Applications, Journal of Materials Chemistry, 2011, 21, 12793.
Chen, Chun-Cheng et al., Properties of Anti-Washout-Type Calcium Silicate Bone Cements Containing Gelatin, J. Mater. Sci. Med (2010) 21:1057-1068; published Nov. 26, 2009.
Chiang, Ting-Yi et al., Physiochemical Properties and Biocompatibility of Chitosan Oligosaccharide/Gelatin/Calcium Phosphate hybrid Cements; Materials Chemistry and Physics 120 (2010) 282-288; published 2009.
Shie, Ming-You et al., The Role of Silicon in Osteoblast-like Cell Proliferation and Apoptosis; Acta Biomaterialia 7 (2011) 2604-2614; published 2011.
Ding, Shinn-Jyh et al., In Vitro Physicochemical Properties, Osteogenic Activity, and Immunocompatibility of Calcium Silicate-Gelatin Bone Grafts for Loan-Bearing Applications; ACS Appl. Mater. Interfaces 2011, 3, 4142-4153; published Sep. 27, 2011.

* cited by examiner

*Primary Examiner* — David Isabella
*Assistant Examiner* — Randy Shay
(74) *Attorney, Agent, or Firm* — WPAT, P.C.; Anthony King

(57) ABSTRACT

A bilayered bone graft device includes a core portion comprising deminernalized gelatin and a shell portion surrounding the core portion. The shell portion includes a calcium silicate and the deminernalized gelatin in a range of 1 to 30 weight percent, and the calcium silicate has a molar ratio of calcium to silicon ranging from 10 to 0.1. The core portion and the shell portion are bound by the deminernalized gelatin without using a binder. In one embodiment of the present invention, the core portion is configured to provide buffering for receiving an insertion, and the shell portion is configured to provide a load-bearing structure.

8 Claims, 3 Drawing Sheets

BILAYERED BONE GRAFT DEVICE

BACKGROUND OF THE INVENTION

1. Technical Field

The present invention relates to a bilayered bone graft device, and more particularly, to a bilayered bone graft device with a composite structure.

2. Background

A variety of ceramic-based bone graft substitutes, such as calcium phosphate and calcium sulfate, have been developed and can provide support, fill voids, and enhance biological repair of skeletal defects. However, their inherent brittleness and fatigue failure limits their application to low-load-bearing or non-load-bearing bones in the human body. Although conventional high-temperature solid-state sintering could be used to fabricate compact high strength ceramic materials, it is not suitable for the preparation of materials containing polymers, drugs, and other bioactive molecules.

Recently, a high strength calcium phosphate ceramic has been developed at room temperature using a cement compaction procedure for bone substitute. However, it must be emphasized that the successful design of a bone substitute material requires an appreciation of the structure of the bone. Bone is a composite structure consisting of apatite nanocrystals incorporated within a collagen matrix, and extensive research has been carried out in the bio-inspired composite composed of a polymer and a ceramic that aptly resembles the morphology and properties of the natural bone.

SUMMARY

One aspect of the present invention provides a bilayered bone graft device with a composite structure.

A bilayered bone graft device according to this aspect of the present invention comprises a core portion including a deminernalized gelatin and a shell portion surrounding the core portion. The shell portion includes a calcium silicate and the deminernalized gelatin in a range of 1 to 30 weight percent, and the calcium silicate has a molar ratio of calcium to silicon ranging from 10 to 0.1. The core portion and the shell portion are bound by the deminernalized gelatin. In one embodiment of the present invention, the core portion is configured to provide buffering for receiving an insertion, and the shell portion is configured to provide a load-bearing structure.

The foregoing has outlined rather broadly the features and technical advantages of the present invention in order that the detailed description of the invention that follows may be better understood. Additional features and advantages of the invention will be described hereinafter, and form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The objectives and advantages of the present invention are illustrated with the following description and upon reference to the accompanying drawings in which.

DETAILED DESCRIPTION

Figure 1:
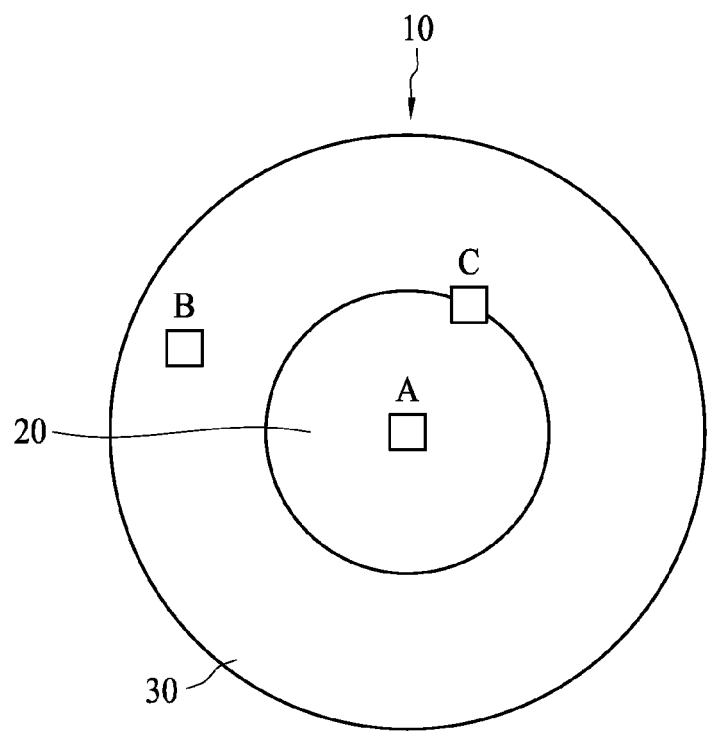
FIG. 1 illustrates a bilayered bone graft device according to one embodiment of the present invention.

FIG. 1 illustrates a bilayered bone graft device 10 according to one embodiment of the present invention. In one embodiment of the present invention, the bilayered bone graft device 10 comprises a core portion 20 including a deminernalized gelatin and a shell portion 30 surrounding the core portion 20. In one embodiment of the present invention, the shell portion 30 includes a mixture of calcium silicate and the deminernalized gelatin.

In one embodiment of the present invention, the concentration of deminernalized gelatin in the shell portion 30 is in a range of 1 to 30 weight percent; preferably, the concentration of deminernalized gelatin is in the range of 2 to 20 weight percent. In one embodiment of the present invention, the calcium silicate has a molar ratio of calcium to silicon ranging from 10 to 0.1; preferably, the calcium silicate has a molar ratio of calcium to silicon ranging from 4 to 0.25.

In one embodiment of the present invention, the shell portion 30 has a compressive strength between 100 and 145 MPa, a modulus between 2.8 and 3.1 GPa, a hardness between 100 and 120 Hv, and a porosity between 10 and 12%. In one embodiment of the present invention, the core portion 20 and the shell portion 30 are bound by the deminernalized gelatin without using a binder.

Figure 2:
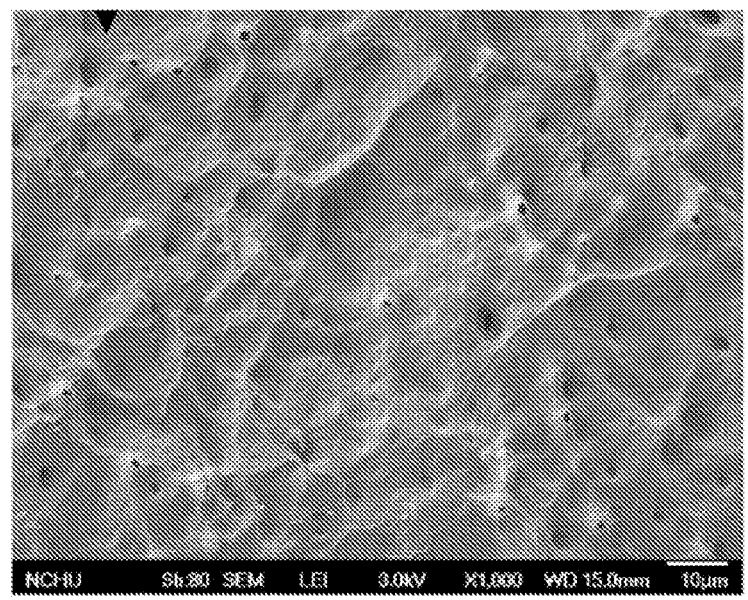
FIG. 2 is a scanning electron microscope (SEM) of the core portion (Portion A)
Figure 3:
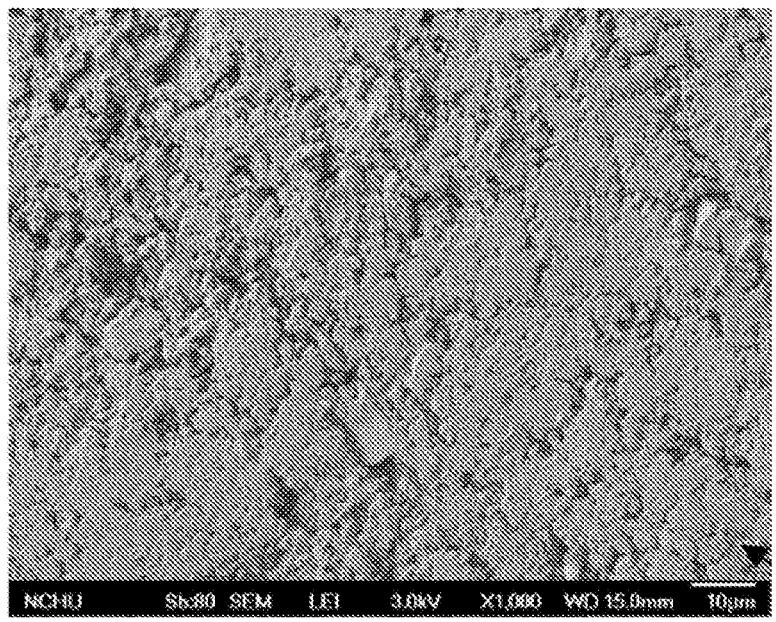
FIG. 3 is a scanning electron microscope of the shell portion (Portion B)
Figure 4:
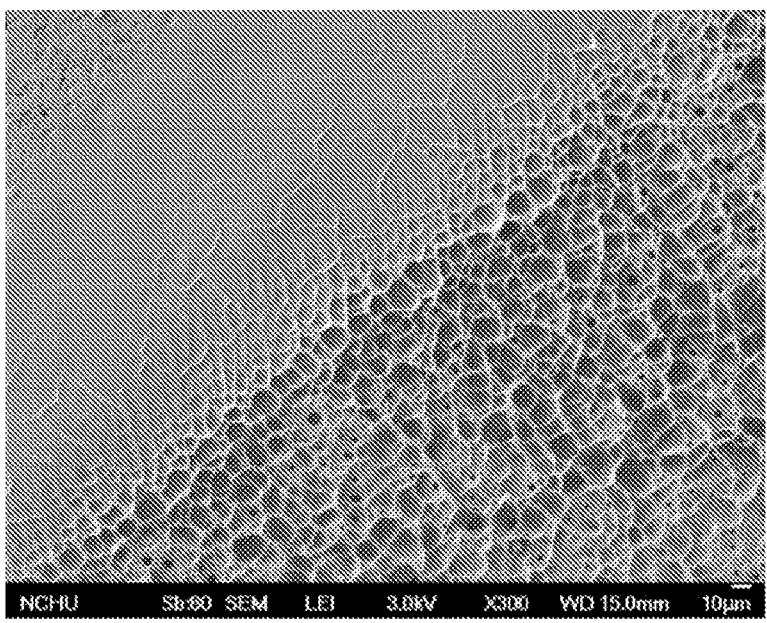
FIG. 4 is a scanning electron microscope of an interface portion (Portion C) between the core portion and the shell portion.
Figure 5:
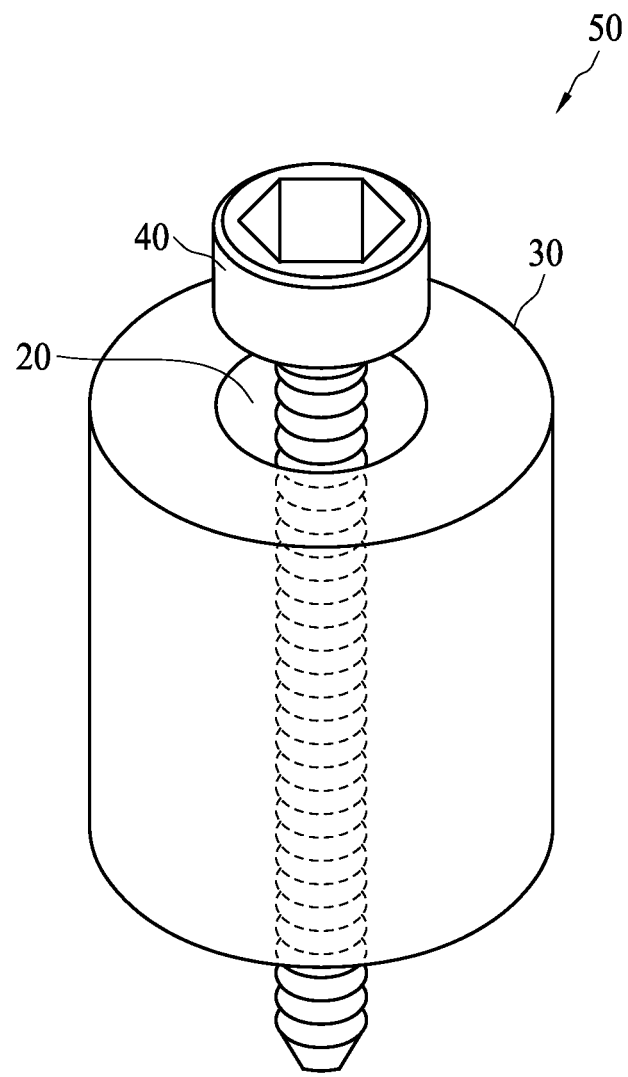
FIG. 5 is a schematic diagram showing an insertion embedded in the core portion of the bilayered bone graft device according to one embodiment of the present invention.

FIG. 2 is a scanning electron microscope (SEM) of the core portion 20 (Portion A); FIG. 3 is a scanning electron microscope of the shell portion 30 (Portion B); and FIG. 4 is a scanning electron microscope of an interface portion (Portion C) between the core portion 20 and the shell portion 30. Obviously, the shell portion 30 is denser than the core portion 20, and the shell portion 30 is configured to provide a load-bearing structure 50, while the core portion 20 is configured to provide buffering for receiving an insertion 40 such as a bolt, as shown in FIG. 5.

Preparation of the Composite for the Shell Portion:

The sol-gel method has been used to prepare the composite for the shell portion. Reagent-grade tetraethyl orthosilicate ($Si(OC_2H_5)_4$, TEOS, 98.0%) (Sigma-Aldrich, St. Louis, Mo.) and calcium nitrate ($Ca(NO_3)_2 \cdot 4H_2O$, 98.0%) (Showa, Tokyo, Japan) were used as precursors for $SiO_2$ and $CaO$, respectively. Nitric acid was used as the catalyst and ethanol was used as the solvent. The general sol-gel procedure, including hydrolysis and aging, was adopted. Briefly, TEOS was hydrolyzed by the sequential addition of 2M $HNO_3$ and absolute ethanol, with one hour of stirring after each addition. $Ca(NO_3)_2 \cdot 4H_2O$ was added to the TEOS solution in an equimolar ratio, and the mixture was stirred for an additional one hour. The molar ratio of ($HNO_3+H_2O$)-TEOS-ethanol was 10:1:10. The sol solution was sealed and aged at 60° C. for one day. After vaporization of the solvent in an oven at 120° C., the dried gel was heated in air to 800° C. at a heating rate of 10° C./min for two hours using a high-temperature furnace and then cooled to room temperature in the furnace to produce a powder. The sintered powders were then ball-milled for 12 hours in ethyl alcohol using a Retsch S100 centrifugal ball mill (Hann, Germany) and dried in an oven at 60° C. Type B gelatin (isoelectric point at pH=4.7-5.2) from bovine skin (Sigma-Aldrich) was weighed and dissolved in distilled water at 60° C. until a homogeneous gelatin solution was obtained. To fabricate the organic-inorganic composite, the calcium silicate powder was mixed with different gelatin solutions (10%, 20%, and 30%) at a powder-to-liquid ratio of 2 mg mL$^{-1}$ using a conditioning mixer (ARE-250, Thinky, Tokyo, Japan), and then the mixture was dried at room temperature for 12 hours. The ratios of gelatin to calcium silicate were approximately 5, 10, and 15% by weight. After grinding the dried powders the hollow compacts were obtained by molding the specimens in a cylindrical stainless steel mold under the applied pressure of 500 MPa for one minute using a uniaxial press, and the compacts were then soaked in deionized water at 60° C. for one hour for hydrothermal processing prior to being dried at 60° C. for two days in an oven.

Preparation of the Composite for the Core Portion:

The gelatin solution was poured into the hollow compact that was rapidly transferred into a freezer at −20° C. for 3 hours, followed by freeze drying over night.

The scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A bilayered bone graft assembly, comprising:
    a core portion including a first demineralized gelatin, the core portion being configured to receive an insertion;
    a shell portion surrounding the core portion, the shell portion including a calcium silicate and a second demineralized gelatin, wherein the second demineralized gelatin is in a range of 2 to 20 weight percent relative to the total weight of the shell portion, the calcium silicate having a molar ratio of calcium to silicon ranging from 10 to 0.1, the shell portion being configured to provide a load-bearing structure;
    wherein the shell portion is prepared using a sol-gel method and hydrothermal processing and has a compressive strength between 100 and 145 MPa, and is adapted for load-bearing bones; and
    wherein the core portion and the shell portion are bound by the first and second demineralized gelatin.

2. The bilayered bone graft assembly of claim 1, wherein the calcium silicate has a molar ratio of calcium to silicon ranging from 4 to 0.25.

3. The bilayered bone graft assembly of claim 1, wherein the shell portion has a hardness between 100 and 120 Hv.

4. The bilayered bone graft assembly of claim 1, wherein the shell portion has a porosity between 10 and 12%.

5. The bilayered bone graft assembly of claim 1 further comprising an insertion, wherein the insertion is embedded in the core portion.

6. The bilayered bone graft assembly of claim 1 further comprising an insertion, wherein the insertion penetrates through the core portion.

7. The bilayered bone graft assembly of claim 1 further comprising an insertion, wherein the insertion is received in the core portion by the first demineralized gelatin.

8. The bilayered bone graft assembly of claim 1, wherein the core portion and the shell portion are bound only by the first and second demineralized gelatin without using any other binder.

* * * * *